United States Patent [19]

Kikuchi et al.

[11] Patent Number: 5,376,380

[45] Date of Patent: Dec. 27, 1994

[54] METHOD OF PRODUCING LIPOSOMAL PRODUCTS FROM FREEZE OR SPRAY-DRIED PREPARATIONS OF LIPOSOMES

[75] Inventors: Hiroshi Kikuchi; Kiyoto Yachi; Hiromi Morita; Sadao Hirota, all of Tokyo, Japan

[73] Assignee: Daiichi Pharmaceutical Co., Ltd.

[21] Appl. No.: 79,842

[22] Filed: Jun. 22, 1993

Related U.S. Application Data

[63] Continuation of Ser. No. 729,268, Jul. 12, 1991, abandoned.

[30] Foreign Application Priority Data

Aug. 21, 1990 [JP] Japan .................................. 2-219735

[51] Int. Cl.$^5$ .................... A61K 9/127; B01J 13/02; B01J 13/20

[52] U.S. Cl. ................................. 424/450; 264/4.1; 264/4.3

[58] Field of Search .................................. 264/4.1, 4.3

[56] References Cited

U.S. PATENT DOCUMENTS

| | | | |
|---|---|---|---|
| 4,673,567 | 6/1987 | Jizomoto | 424/450 |
| 4,769,250 | 9/1988 | Forssen | 424/491 X |
| 4,946,683 | 8/1990 | Forssen | 424/422 |
| 5,059,421 | 10/1991 | Loughrey et al. | 424/450 X |

*Primary Examiner*—L. S. Kishore
*Attorney, Agent, or Firm*—Sughrue, Mion, Zinn, Macpeak & Seas

[57] ABSTRACT

A method of producing liposomal products which comprises treating a positively or negatively charged, freeze- or spray-dried liposomal preparation with an aqueous solution of a drug charged oppositely to the charge of the liposomes.

2 Claims, No Drawings

METHOD OF PRODUCING LIPOSOMAL PRODUCTS FROM FREEZE OR SPRAY-DRIED PREPARATIONS OF LIPOSOMES

This is a continuation of application Ser. No. 07/729,268 filed Jul. 12, 1991, now abandoned.

FIELD OF THE INVENTION

This invention relates to a method of producing liposomal products with a high drug encapsulation efficiency which comprises treating a positively or negatively charged, freeze- or spray-dried liposomal products with an aqueous solution of a drug charged oppositely to the charge of the liposomes.

BACKGROUND OF THE INVENTION

Liposomes are widely used as models of biomembranes. Furthermore, they have recently been energetically investigated as a typical example of the drug delivery system (DDS).

However, when a water-soluble drug is encapsulated in liposomes by the conventional method, the encapsulation efficiency of drugs is generally low (in most cases 0.1 to 20%). There are two reasons: i) the mode of encapsulation of a low molecular water-soluble drug in liposomes basically consists in distribution of the drug in the same concentration between the inner aqueous phase and outer aqueous phase of the liposomes and ii) for making liposomes stable as separate particles in an aqueous medium, it is necessarily required that the aqueous medium be present externally to liposomes as a dispersion medium therefor.

In view of the above, it has been considered very difficult to raise the drug encapsulation efficiency, in particular to a level close to 100%, when a water-soluble drug is caused to be encapsulated in liposomes.

Known methods for increasing the encapsulation efficiency of such a water-soluble drug or a drug having a small affinity for membranes include, among others, a) a reversed phase evaporation method (Proceedings of National Academy Sciences of U.S.A., 75, 4194, 1978), b) a chemical modification of drugs themselves (International Journal of Pharmaceutics, 14, 191, 1983; Journal of Pharmacobiodynamics, 7, 120, 1984; Chemical and Pharmaceutical Bulletin, 36, 3574, 1988), c) a use of other auxiliaries or the like (Journal of Pharmaceutical Sciences, 71, 958, 1982; Drug Development and Industrial Pharmacy, 10, 613, 1984), d) a modification of the properties of liposomal membranes themselves (Biochimica et Biophysica Acta, 812, 66, 1985; Biochimica et Biophysica Acta, 857, 123, 1986), and e) a use of a phospholipid having a charge opposite to the charge of the drug (Biochemical and Biophysical Research Communications, 107, 136, 1982; International Journal of Pharmaceutics, 17, 135, 1983; U.S. Pat. No. 4,769,250.

The prior art methods such as mentioned above are not satisfactory when a drug is to be efficiently encapsulated in liposomes.

Furthermore, any method has been found as yet for causing a drug to be encapsulated in liposomes at a high encapsulation efficiency by merely adding an aqueous solution of the drug to a freeze-dried (lyophilized) or spray-dried liposomal preparation not yet containing the drug.

SUMMARY OF THE INVENTION

Intensive investigations made by the present inventors in an attempt to overcome the above problems have now led to completion of the present invention.

That is, object of this invention is to provide liposomal products having a very high drug encapsulation efficiency which can be produced with good reproducibility, in spite of using liposomes containing no any drug.

The above object of this invention can be accomplished by a method of producing liposomal products with a high drug encapsulation efficiency which comprises treating positively or negatively charged, freeze- or spray-dried liposomal products with an aqueous solution of a drug charged oppositely to the charge of the liposomes.

DETAILED DESCRIPTION OF THE INVENTION

The positively or negatively charged, freeze- or spray-dried liposomal products to be used in this invention are produced by first preparing an aqueous dispersion of charged liposomes which do not contain any drugs in advance and then subjecting the dispersion to freeze-drying or spray-drying.

For preparing an aqueous dispersion of positively charged liposomes, a positively charged lipid (cationic lipid) is used as an essential liposomal membrane component. Examples of such lipid are basic lipids such as stearylamine and basic amino acid derivative surfactants such as $N^{\alpha}$-acyl-L-arginines. Generally, these cationic lipids are used in combination with one or more other main liposomal membrane components, such as phosphatidylcholines or sphyngomyelins. The raio of addition of the cationic lipids is not particularly limited. Preferably, however, they are suitably used in a mole percent of 10 to 30% to the total amount of liposomal membrane components.

For preparing an aqueous dispersion of negatively charged liposomes, a negatively charged lipid (anionic lipid) is used as a liposomal membrane component. The typical examples thereof include acidic phospholipids such as phosphatidylserines, natural source-derived phosphatidylglycerols, dimyristoylphosphatidylglycerol, dipalmitoylphosphatidylglycerol, cardiolipins, phosphatidylinositols or phosphatidic acids, sialic acid-containing gangliosides such as ganglioside $GM_1$ or ganglioside $GM_3$, acid lipids such as dicetyl phosphate, acidic amino acid derivative surfactants such as N-acyl-L-glutamic acids, fatty acids such as oleic acid or stearic acid, and the like. Generally, these anionic lipids are used in combination with one or more other main liposomal membrane components such as phosphatidylcholines or sphingomyelins. The ratio of addition of the anionic lipids is not particularly limited. Preferably, however, they are suitably used in a mole percent of 10 to 30% to the total amount of liposomal membrane components. As the acidic phospholipids such as phosphatidylserines, phosphatidylglycerols or phosphatidylinositols can by themselves form liposomes and these may be used in a mole percent of 10 to 100% to the total amount of liposomal membrane components.

It is desirable to understand that the anionic lipids or cationic lipids (hereinafter collectively referred to as "charged lipids") to be employed in this invention do not include within the meaning thereof phosphatidylcholines, sphingomyelins and the like, which are used as main components of liposomal membranes. This is because although these have, within their molecule, a cationic choline group and an anionic phosphoric acid group in positions close to each other, they have no charge as the whole molecule in the neutral pH region.

In addition to the above-mentioned charged lipids and main components of liposomal membrane (phosphatidylcholines, sphingomyelins, etc.), sterols, such as cholesterol, may be added as membrane stabilizers, and/or α-tocopherol and the like as antioxidants. The ratio of addition of these additives is not particularly limited. Suitably, however, sterols as stabilizers are added in a mole percent of 0 to 0%, preferably 30 to 55%, to the total amount of liposomal membrane components. Antioxidants such as α-tocopherol are suitably used in a mole percent of 0 to 20%, preferably about 1%, to the total amount of liposomal membrane component.

In some instances, a cationic lipid such as mentioned above and an anionic lipid such as mentioned above may be used combinedly for liposome formation. In such cases, the charge, as a whole, of the liposomes in the aqueous dispersion should be either positive or negative.

The production of aqueous dispersions of positively or negatively charged liposomes is described in the following.

According to the various known methods, for example the method disclosed in Journal of Molecular Biology, 13, 238 (1965), the liposomal membrane components mentioned above are first dissolved in an appropriate organic solvent, such as chloroform or methanol, and then the solvent is distilled off to cause formation of a lipid film. To the lipid film is then added an aqueous medium to thereby cause hydration and swelling. Dispersion is further effected using a mixer such as a vortex mixer or an agitating/homogenizing mixer to give an aqueous dispersion of positively or negatively charged liposomes containing no drug. In this step, when the temperature of the aqueous medium is higher, a higher emulsification efficiency will be obtained. Such aqueous liposomal dispersion may also be produced by any other known method of liposome production, for example the procedure disclosed in Annual Review of Biophysics and Engineering, 9, 467 (1980).

For assuring the stability of liposomes and drugs, the aqueous medium should generally have a pH of about 3 to 8. For the stability of liposomes, the pH should preferably be 6 to 8. The typical examples of the acid to be used for such pH adjustment include a monovalent inorganic acid such as hydrochloric acid, nitric acid or hydrobromic acid, or a monovalent organic acid such as lactic acid, glyceric acid or acetic acid. Hydrochloric acid and lactic acid are preferred, however. The base for such pH adjustment includes monovalent hydroxides such as potassium hydroxide, sodium hydroxide and lithium hydroxide, and monovalent amines such as triethylamine, trimethylamine, diisopropanolamine, diethanolamine, triethanolamine, tetramethylamine and tris(hydroxymethyl)aminomethane. Among these, potassium hydroxide and sodium hydroxide are preferred. Furthermore, acids containing a divalent or trivalent ion, such as potassium primary phosphate, sodium secondary phosphate and sodium carbonate, may also be used.

The electrolyte ion concentration in the aqueous medium should desirably be as low as possible and, generally, the total concentration of ions except the drug should suitably be not more than about 40 mM.

The osmotic pressure of the product mixture resulting from addition of an aqueous drug solution to the freeze- or spray-dried liposomal preparation in accordance with the invention should be preferably be equal or close to the osmotic pressure of body fluids. Generally, an isotonizing agent, for example a polyhydric alcohol such as glycerol or propylene glycol, or a saccharide such as mannitol, sucrose, glucose or lactose, should be added to said aqueous medium.

The particle size of the thus-obtained liposomes is generally 50 to 1,000 nm, preferably 60 to 300 nm, more preferably 70 to 200 run, although said particle size is not critical. Particle size control can be made in the conventional manner such as emulsifying treatment using an ultrasonicator or a Manton-Gaulin homogenizer and extrusion treatment disclosed in Annual Review of Biophysics and Engineering, 9, 467 (1980).

Furthermore, the number of membranes in the liposomes according to the invention is not limited to any particular value or range. The number of membranes can be used as desired. The number can be controlled by any of known conventional techniques such as the above emulsifying treatment disclosed in Annual Review of Biophysics and Engineering, 9, 467 (1980).

The thus-obtained aqueous dispersion of liposomes can be processed by a conventional method to give a freeze- or spray-dried preparation. Thus, for instance, when a freezedried preparation is desired, the above-mentioned aqueous liposomal dispersion is distributed into vials or other containers and then subjected to lyophilization in a conventional manner. Desirable lyophilization conditions are as follows: rapid freezing should be attained at a freezing temperature of −5° to −80° C., preferably −30° to −40° C. and water should be sublimed at a reduced pressure of 0.1 tort or below. When a spray-dried preparation is desired, the above-mentioned aqueous liposomal dispersion is spray-dried for solvent removal and the powder obtained is distributed under aseptic conditions into vials or other appropriate containers, which are then sealed. Spray-drying conditions which are desirable include an inlet temperature of 110° to 200° C., preferably 120° to 150° C.

To the freeze- or spray-dried liposomal preparation obtained in the above manner, there is added an aqueous solution of a drug charged oppositely to the liposomes, whereby an aqueous liposomal dispersion with a high drug encapsulation efficiency can be produced. When the amount of the drug in the aqueous drug solution to be added is not more than ½, preferably not more than ⅓, on the ion equivalent basis relative to the oppositely charged liposomes or, more precisely, relative to the charged lipid involved in charging of the liposomes, a higher drug encapsulation efficiency can be attained. The electrolyte ion concentration in the aqueous drug solution should desirably be as low as possible. More desirably, the total electrolyte ion concentration in the aqueous liposomal dispersion resulting from addition of the aqueous drug solution should be not more than 40 mM.

The positively charged or cationic group-containing drug to be used in this invention includes, but is not limited to, anticancer agents, such as daunorubicin, doxorubicin, aclarubicin, 4-O-tetrahydropranyladriamycin, 4-epiadriamycin, 4-demethoxydaunomycin, mitomycin C, bleomycin and methotrexate; antibiotics, such as ampicillin, amoxicillin, cephalexin, cefaclor, gentamicin, sisomicin, streptomycin, kanamycin, amikacin and amphotericin B; chemotherapeutic agents, such as sulfisomidine, sulfadimethoxine, sulfamonomethoxine, isoniazide and ofloxacin; drugs for general use, such as tranexamic acid and glutathione; polypeptides having a basic amino acid moiety within the molecule, such as neocarzinostatin and insulin; bioactive agents having a basic amino acid moiety within the molecule, such as interferons, tumor necrosis factor (TNF), epithelial growth factor (EGF) and interleukins; and so on. The cationic group which these drugs have is not limited but may be a primary amine, secondary amine, tertiary amine or cyclic amine moiety.

The negatively charged or anionic group-containing drug to be used in this invention includes, but is not limited to, anticancer agents such as methotrexate; antibiotics, such as benzylpenicillin, ampicillin, amoxicillin, piperacillin, cephaloridine, cephalothin, cafazolin, cefamandole, cefotaxime, caphalexin, cefoxitin, cefmetazole and cefotetan; chemotherapeutic agents such as sulfisomidine, sulfadimethoxine, sulfamonomethoxine, nalidixic acid, ofloxacin and enoxacin; drugs for general use, such as tranexamic acid, glutathione and aspirin; polypeptides having an acidic amino acid moiety within the molecule, such as neocarzinostatin and insulin; bioactive agents having an acidic amino acid moiety within the molecule, such as interferons, tumor necrosis factor (TNE), epithelial growth factor (EGF) and interleukins; and sulfated sugar-containing polysaccharides, such as heparin, chondroitinsulfuric acid and dextransulfuric acid. The anionic group in the drugs mentioned above is not limited but may be a carboxylic, carbonic acid, phosphoric acid, sulfonamide, sulfuric acid, sulfurous acid, nitric acid or nitrous acid group, for instance.

Among the drugs such as mentioned above, anthracycline anticancer antibiotics, such as daunorubicin and doxorubicin (adriamycin), and nalidixic acid and the like, for instance, have, within their molecule, only one amino group (in the former) or only one carboxyl group (in the latter), so that they can be regarded as drugs having a monovalent cationic group or drugs having a monovalent anionic group, respectively. In the case of fosfomycin, which has one phosphoric acid group having the character of a bivalent anion within their molecule, it can be regarded as a drug having divalent anionic group. Gentamicin, which has three amino groups within its molecule, can be regarded as a drug having trivalent cationic group, and dextransulfuric acid, which has a number of sulfuric acid groups and is a polysaccharide having an average molecular weight of about 7,500 with 0 to 2 sulfuric acid groups per glucose unit, as a drug having a polyvalent anionic groups.

In the case of ampicillin, sulfadimethoxine, methotrexate and the like, their molecule has the same number of cationic groups and anionic groups identical in valency at sites remote from each other (one cationic group and one anionic group identical in valency in the former two and two cationic groups and two anionic groups identical in valency in methotrexate). Drugs of this kind may be regarded either as cationic group-containing drugs or as anionic group-containing drugs in classifying them in the practice of the invention.

Thus, for instance, ampicillin and sulfadimethoxine may be regarded as drugs having a monovalent cationic group or as drugs having a monovalent anionic group while methotrexate may be regarded as a drug having a divalent cationic group or as a drug having a divalent anionic group.

Similarly, drugs, e.g. polypeptides such as neocarzinostatin, insulin, etc., interferon and so on, having a cation moiety or moieties such as basic amino acid residues as well as an anion moiety or moieties such as sialic acid or acidic amino acid residues, may be classified either as cationic group-containing drugs or as anionic group-containing drugs. If, however, a drug is to be regarded as a cationic one for reason of greater contribution of the cationic group to the charged state of the molecule when its molecule is considered as a whole, such drug should desirably be classified as a cationic group-containing drug. In a reversed case, the drug should desirably be classified among anionic group-containing drugs. In evaluating the valence of the ionic group which such drug should be regarded as having, the total amount of equivalent numbers of the ions on the charge side greater in contribution may be employed.

The following description will be further illustrative of the effect of the quantity of the anionic or cationic lipid (charged lipid) used and the effect of the kind of charged lipid. In the case of doxorubicin (monovalent cation), for instance, an anionic monovalent charged lipid, such as a phosphatidylglycerol (monovalent anion) or phosphatidylserine (monovalent anion), should recommendably be used in a molar ratio of not less than 2, preferably not less than 3, relative to the drug; in the case of fosfomycin (having one divalent anion), a cationic monovalent charged lipid, such as stearylamine (monovalent cation), in a molar ratio of not less than 4, preferably not less than 6, relative to the drug; and in the case of gentamicin (having three monovalent cations), a phosphatidylglycerol in a molar ratio of not less than 6, preferably not less than 9, relative to the drug.

Generally, as mentioned above, the encapsulation efficiency of an ionic drug into liposomes can be increased by using the charged lipid in an amount of not less than 2, preferably not less than 3 on the ionic equivalent basis relative to the used drug.

The present invention makes it possible to produce liposomes with a high drug encapsulation efficiency that has never been attained in the prior art. The invention thus provides an excellent method of producing liposomes with a high drug encapsulation efficiency.

Furthermore, the method of the invention is simple and easy to apply and, accordingly, is also an excellent method of producing liposomes with a high encapsulation efficiency of a drug which is unstable against heat and/or mechanical shearing force on the occasion of emulsification, stirring or the like, for example a polypeptide drug, such as neocarzinostatin, insulin, interferon, tumor necrosis factor, epithelial growth factor, or interleukin.

The present invention is now illustrated in greater detail by way of the following examples, but it should be understood that the present invention is not deemed to be limited thereto. The preparative procedures, analytical methods and so forth which are basically identical throughout the examples, are first described in the following.

EXAMPLES 1 TO 9

(1) Method of preparing an aqueous dispersion of empty liposomes:

The lipid membrane components were placed in a glass vessel and once completely dissolved in a mixture of chloroform and metanol. The organic solvents were then distilled off under a nitrogen gas stream or under reduced pressure, followed by further drying in a desiccator (under reduced pressure). Then, buffer solution substantially isotonized to the biological osmotic pressure using sucrose was added thereto and the whole was agitated with a vortex mixer or agitating/homogenizing mixer with gentle warming to give a crude dispersion of liposomes.

This crude liposome dispersion was further subjected to filtration under high pressure through a polycarbonate membrane filter having a specific pore size to make liposomes more uniform in particle size.

(2) Method of producing a freeze-dried empty-liposomal preparation:

The aqueous liposomal dispersion finally obtained by the above procedure (1) was distributed in certain amounts into vials. The vials were half-stoppered and placed in a freeze drier cooled in advance to a shelf temperature of −40° C. and the samples were lyophilized under ordinary lyophilization conditions. After drying, the atmosphere within the vials was replaced with nitrogen and the vials were stoppered. Thus was obtained a freeze-dried preparation of empty liposomes.

(3) Method of producing a spray-dried liposomal preparation:

The aqueous liposomal dispersion obtained by the above procedure (1) was fed to a spray drier for distilling off the solvent. The dried powder thus obtained was distributed in specific amounts into vials, which were then stoppered. Thus was obtained a spray-dried liposomal preparation.

(4) Method of producing drug-containing liposomes:

An aqueous dispersion of drug-containing liposomes was produced by adding, for reconstitution, an aqueous solution of a drug at a certain concentration to the freezedried or spray-dried liposomal preparation obtained as mentioned above.

(5) Particle size measurement:

For each aqueous liposomal dispersion obtained by reconstitution from the freeze-dried or spray-dried liposomal preparation obtained by the above procedure (2) or (3) by adding distilled water for injection thereto, and for each aqueous dispersion of drug-containing liposomes as obtained by the above procedure (4), liposomal particle size measurement was carried out by the quasi-elastic light scattering method. The results obtained are shown in Table 1.

(6) Drug encapsulation efficiency measurement:

Each aqueous dispersion of drug-containing liposomes as obtained by the above procedure (4) was subjected to ultracentrifugation to give a liposomal fraction and the encapsulation efficiency of the drug in liposomes was determined using a spectrophotometer. The results obtained are shown in Table 1.

TABLE 1

Characteristics of liposomal dispersions resulting from addition of an aqueous drug solution to freeze-dried empty liposomes or spray-dried empty liposomes

| Example No. | Lipid Composition [mM] | | | Aqueous Medium | | Scale of preparation (ml) | Form of Empty Liposomal Preparation (amount pervial) | Particle Size after Reconstitution with Distilled Water (nm) | Aqueous Drug Solution for Reconstituting of Dried Empty Liposomes | | | Charged Lipid/Drug Charge Equivalent Ratio | After Reconstitution with Aqueous Drug Solution | | |
|---|---|---|---|---|---|---|---|---|---|---|---|---|---|---|---|
| | Charged Lipid (charge) | Cholesterol | Other lipid | Component | | | | | Drug (charge) | Medium for Drug | Drug Concentration | | Appearance | Particle size (nm) | Encapsulation Efficiency of Drug (%) |
| Example 1 | egg yolk PG (negative) 6.0 | 10.0 | egg yolk PC 4.0 | 10% sucrose | | 50 | freeze-dried (2 ml) | 121 | doxorubicin hydrochloride (positive) | distilled water | 0.75 mg/ml | 4.6 | good | 114 | 93.7 |
| Control 1 | egg yolk PG (negative) 2.0 | 10.0 | egg yolk PC 8.0 | 10% sucrose | | 50 | freeze-dried (2 ml) | 129 | doxorubicin hydrochloride (positive) | distilled water | 0.75 mg/ml | 1.5 | good | 133 | 47.9 |
| Example 2 | egg yolk PG (negative) 6.0 | 10.0 | — | 10% sucrose | | 50 | freeze-dried (2 ml) | 182 | doxorubicin hydrochloride (positive) | distilled water | 0.75 mg/ml | 7.7 | good | 170 | 96.5 |
| Control 2 | — | 10.0 | egg yolk PC 10.0 | 10% sucrose | | 50 | freeze-dried (2 ml) | 190 | doxorubicin hydrochloride (positive) | distilled water | 0.75 mg/ml | 0 | good | 184 | 8.6 |
| Example 3 | DMPG (negative) 15.2 | 16.0 | egg yolk PC 2.7 | 10% sucrose | | 20,000 | spray-dried (10 ml) | 103 | doxorubicin hydrochloride (positive) | distilled water | 1.0 mg/ml | 8.8 | good | 106 | 99.0 |
| Example 4 | Stearylamine (positive) 7.5 | 17.5 | egg yolk | 10% sucrose PC 25.0 | | 100 | freeze-dried (2 ml) | 99 | bilirubin oxidase (negative) | distilled water | 10 U/ml | — | good | 114 | 84.2 |
| Example 5 | egg yolk PG (negative) 10.0 | 10.0 | — | 10% sucrose | | 200 | freeze-dried (2 ml) | 369 | γ-interferon (positive) | distilled water | 5 × 10 U/m | — | good | 354 | 89.3 |
| Example 6 | egg yolk PG (negative) 10.0 | 10.0 | — | 10% sucrose | | 200 | freeze-dried (2 ml) | 369 | daunorubicin hydrochloride (positive) | distilled water | 0.75 mg/ml | 7.7 | good | 285 | 91.3 |
| Control 3 | egg yolk PG (negative) 4.0 | 10.0 | egg yolk PC 6.0 | 10% sucrose | | 500 | freeze-dried (2 ml) | 154 | daunorubicin hydrochloride | distilled water | 2.0 mg/ml | 1.1 | aggregation | unmeasurable | |

TABLE 1-continued

Characteristics of liposomal dispersions resulting from addition of an aqueous drug solution to freeze-dried empty liposomes or spray-dried empty liposomes

| Example No. | Lipid Composition [mM] Charged Lipid (charge) | Cholesterol | Other lipid | Aqueous Medium Component | Scale of preparation (ml) | Form of Empty Liposomal Preparation (amount pervial) | Particle Size after Reconstitution with Distilled Water (nm) | Drug (charge) | Medium for Drug | Drug Concentration | Charged Lipid/Drug Charge Equivalent Ratio | After Reconstitution with Aqueous Drug Solution Appearance | Particle size (nm) | Encapsulation Efficiency of Drug (%) |
|---|---|---|---|---|---|---|---|---|---|---|---|---|---|---|
| Example 7 | egg yolk PG (negative) 20.0 | 50.0 | egg yolk PC 30.0 | 10% sucrose | 200 | freeze-dried (2 ml) | 257 | pirarubicin chloride (positive) | distilled water | 2.0 mg/ml | 6.3 | good | 326 | 95.0 |
| Control 4 | egg yolk PG (negative) 4.0 | 10.0 | egg yolk PC 6.0 | 10% sucrose | 500 | freeze-dried (2 ml) | 154 | pirarubicin (positive) | distilled water | 2.0 mg/ml | 1.3 | aggregation | unmeasurable | |
| Example 8 | egg yolk PG (negative) 10.0 | 10.0 | — | 10% sucrose | 200 | freeze-dried (2 ml) | 369 | epirubicin hydrochloride (positive) | distilled water | 0.75 mg/ml | 7.7 | good | 481 | 96.0 |
| Control 5 | egg yolk PG (negative) 4.0 | 10.0 | egg yolk PC 6.0 | 10% sucrose | 500 | freeze-dried (2 ml) | 154 | epirubicin hydrochloride (positive) | distilled water | 2.0 mg/ml | 1.1 | aggregation | unmeasurable | |
| Example 9 | egg yolk PG (negative) 20.0 | 50.0 | egg yolk PC 30.0 | 10% sucrose | 200 | freeze-dried (2 ml) | 257 | amphotericin B (positive) | distilled water | 5.0 mg/ml | 9.1 | good | 223 | 99.2 |
| Example 10 | DMPG (negative) 15.2 | 16.0 | egg yolk PC 2.7 | 10% sucrose | 20,000 | freeze-dried (10 ml) | 110 | amikacin (positive) | distilled water | 1.0 mg/ml | 2.2 | good | 85 | 97.5 |
| Example 11 | DMPG (negative) 15.2 | 16.0 | egg yolk PC 2.7 | 10% sucrose | 20,000 | freeze-dried (10 ml) | 110 | streptomycin sulfate (positive) | distilled water | 1.0 mg/ml | 3.7 | good | 105 | 92.1 | egg yolk PG: egg yolk phosphatidylglycerol;
egg yolk PC: egg yolk phosphatidylcholine;
DMPG: Dimyristoylphosphatidylglycerol.

As is evident from Table 1, it was confirmed that liposomal preparations with a high drug encapsulation efficiency can be produced by the method of this invention and, furthermore, that the liposomal preparations produced have a very well controlled particle size distribution.

While the invention has been described in detail and with reference to specific embodiments thereof, it will be apparent to one skilled in the art that various changes and modifications can be made therein without departing from the spirit and scope thereof.

What is claimed is:

1. A method of producing liposomal products which comprises contacting a positively or negatively charged, freeze- or spray-dried preparation of liposomes with an aqueous solution of a drug charged oppositely to the charge of the liposomes, wherein the total concentration of ions, excluding the charged drug, in the aqueous solution of a charged drug is not more than 40mM, and wherein the ratio of the amount of charged lipid in the preparation of liposomes to the total amount of liposomal membrane components is 10 to 30 mole percent.

2. A method of producing liposomal products as claimed in claim 1, wherein charged lipid in the preparation of liposomes is present in an amount of not less than 2, on an ionic equivalent basis relative to the drug.

* * * * *